US00PP14739P2

(12) United States Plant Patent
Chandler

(10) Patent No.: US PP14,739 P2
(45) Date of Patent: Apr. 27, 2004

(54) 'STRAWBERRY FESTIVAL' STRAWBERRY PLANT

(50) Latin Name: *Fragaria×ananassa*
Varietal Denomination: Strawberry Festival

(75) Inventor: Craig K. Chandler, Temple Terrace, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 09/562,439

(22) Filed: May 1, 2000

(51) Int. Cl.[7] ..... A01H 5/00

(52) U.S. Cl. ..... Plt./208

(58) Field of Search ..... Plt./208

*Primary Examiner*—Bruce R. Campell
*Assistant Examiner*—W C Haas

(57) ABSTRACT

A new and distinct variety of strawberry (*Fragaria× ananassa*), which originated from seed produced by a hand-pollinated cross between 'Rosa Linda' and 'Oso Grande'. The new strawberry, named 'Strawberry Festival', is distinguished by the numerous runners it produces in the fruiting field, the long pedicels attached to its fruit, and the production of fruit that are flavorful, firm fleshed, deep red on the outside, bright red on the inside, conically shaped, and have large, showy calyces when grown in Dover, Fla. or other areas that have a subtropical climate similar to that of Dover.

2 Drawing Sheets

Botanical designation: *Fragaria×ananassa* Duchesne.

BACKGROUND OF THE NEW VARIETY

The present invention relates to a new and distinct variety of strawberry (*Fragaria×ananassa* Duchesne) plant which is named 'Strawberry Festival' and more particularly to a strawberry plant that is distinguished by its production of fruit that are flavorful, firm fleshed, deep red on the outside, bright red on the inside, conically shaped, and have large, showy calyces. Asexual propagation was performed at Dover, Fla. where the selection was made and plants were tested. Contrast is made to 'Sweet Charlie' (U.S. Plant Pat. No. 8,729) and 'Camarosa' (U.S. Plant Pat. No. 8,708), standard varieties, for reliable description. This new variety is a promising candidate for commercial success in that it will provide Florida growers with a variety that produces fruit that are attractive and flavorful, and maintains these qualities during and after long-distance shipment.

ORIGIN OF THE VARIETY

This strawberry plant (genotype) originated as a single plant in a strawberry breeding plot at Dover, Fla. The seed parent was 'Rosa Linda' (U.S. Plant Pat. No. 9,866), a strawberry variety with a desirable fruit shape and high early season yield potential. The pollen parent was 'Oso Grande' (U.S. Plant Pat. No. 6,578), a variety that can produce large, firm fiuit. The seeds resulting from the controlled hybridization were germinated in a greenhouse and the resulting seedlings were planted and allowed to produce daughter plants by asexual propagation (i.e. by runners). Two daughter plants were asexually reproduced from each seedling and were transplanted to raised beds, where they fruited. 'Strawberry Festival' strawberry was selected for further evaluation. 'Strawberry Festival' was selected from among.248 sibling genotypes as the 41st selection of the 1995–96 season, and thus was designated FL 95-41. It has been asexually propagated by runners, annually, and further test plantings have established that the vegetative and fruit characteristics of the propagules are identical to the initial two daughter plants.

SUMMARY THE VARIETY

'Strawberry Festival', when grown in a subtropical fall and winter climate, is set apart from all other strawberry plants by a combination of the following characteristics: vigorous plant that has a tendency to produce numerous runners in the fruiting field; long pedicels (Pedicels attached to mature primary fruit are 188 to 240 mm long.); fruit that are deep red on the outside, bright red on the inside, conically shaped, and have large, showy calyces.

BRIEF DESCRIPTION OF THE DRAWINGS

The first photograph illustrates typical 'Strawberry Festival' fruit.

The second photograph illustrates a typical 'Strawberry Festival' plant when grown in typical outdoor conditions.

DETAILED BOTANICAL DESCRIPTION

The following botanical description is that of the variety grown under the typical outdoor ecological conditions prevailing at Dover, Fla., USDA Zone 9a. Plants described were 3 to 6 months from planting 8 to 10 week-old bare root transplants into a production field. Colors are described using the Pantone® Color Formula Guide.

'Strawberry Festival' is a short day cultivar. It has a vigorous plant that tends to produce numerous runners if planted in early October in central Florida. Average height and width for mature plants is 23 cm and 30 cm respectively. Average petiole length and diameter is 120 mm and 3.5 mm respectively, and petioles have a medium pubescence. Average length and breadth of terminal leaflets is 78 and 73 mm respectively. Average length and breadth of secondary leaflets is 69 and 72 mm respectively. Leaflet margins are crenate and average 21 serrations per terminal leaflet, and 26 per secondary leaflet. The upper leaf surface is a dark grey green (Pantone® 575); the lower leaf surface is a light grey green (Pantone® 5767); and the petiole is a medium yellow green (Pantone® 583). Flowers open at or below canopy height, and have an average of 5.3 petals and 24 stamens. Individual petals have a length and width of 1.1 cm. The diameter of the corolla (i.e. the petals collectively) is 2.8 cm. The color of the calyx is yellow green (Pantone® 371). Pedicels attached to mature primary fruit are 188 to 240 mm long, 2.5 mm in diameter, and yellow green (Pantone® 384), with branching of the inflorescence usually occurring very close to the crown. Mean fruit weight is similar to that of 'Sweet Charlie' (Table 1). Primary fruit are wedge-shape to conic (weighing 25–35 g); whereas secondary and tertiary fruit are mostly conic (weighing 15–25 g). The external color of fully mature fruit is deep red and glossy (Pantone® 188); internal color is a bright red (Pantone® 179). The achenes are generally light gold (Pantone® 458) and level with the fruit surface. The calyx is large and showy. Fruit of 'Strawberry Festival' are very firm, with moderate juiciness and excellent flavor (Table 2). A panel of tasters rated 'Strawberry Festival' as having more strawberry aroma than 'Camarosa', but less strawberry aroma than 'Sweet Charlie'. 'Strawberry Festival' also exhibits peach aroma similar to 'Sweet Charlie', and greater peach aroma than 'Camarosa'. The % soluble solids reading of 'Strawberry Festival' is a mean of 7.4%, which is comparable to 'Camarosa' (7.4%) and 'Sweet Charlie' (7.5%). The titratable acidity of 'Strawberry Festival' is 0.79%, while the titratable acidities of 'Camarosa' and 'Sweet Charlie' measure 0.86% and 0.65%, respectively. The penetrometer reading of 'Strawberry Festival' in kg/force is 0.40, while the penetrometer readings of 'Camarosa' and 'Sweet Charlie' (measured in the same kg/force units) are 0.35 and 0.26, respectively. The preferred planting date for 'Strawberry Festival' is October 5 to October 15 in central Florida. In replicated plot trials at Dover, Fla., 'Strawberry Festival' produced total marketable yields as high or higher than those of 'Sweet Charlie', and as high as 'Camarosa' in 1997–98, but not as high as those of 'Camarosa' in 1998–99 and 1999–00 (Table 1). In two commercial fields in the Dover/Plant City area in 1999–00, 'Strawberry Festival' had a fruiting pattern and yield similar to that of 'Camarosa'. In observational plots at Live Oak, Fla. (north central Florida), 'Strawberry Festival' has been less vigorous and had lower fruit yields than 'Camarosa', but has been more vigorous and had higher fruit yields than 'Sweet Charlie'. 'Strawberry Festival' is susceptible to anthracnose fruit rot (caused by *Colletotrichum acutatum* Simmonds), Colletotrichum crown rot (caused by *Colletotrichum gloeosporodies* Penz.), and angular leaf spot (caused by *Xanthomonas fragariae* Kennedy & King); therefore we recommend that fruit growers choose their transplant source carefully to avoid starting off their season with infected plants. 'Strawberry Festival' is less susceptible than 'Sweet Charlie' to Botrytis fruit rot (caused by *Botrytis cinerea* Pers.ex Fr.) and less susceptible than 'Camarosa' to powdery mildew (caused by *Sphaerotheca macularis* [Wallr. ex Fr.] Jacz. f. sp. *fragariae*). 'Strawberry Festival's relative susceptibility to the twospotted spider mite (*Tetranychus urtricae* Koch) is unknown, but a serious infestation has not yet been observed. DNA banding patterns for 'Strawberry Festival', 'Sweet Charlie', 'Camarosa', 'Rosa Linda', and 'Oso Grande' are presented in Table 3.

TABLE 1

Performance of 'Strawberry Festival' strawberry compared with two standard cultivars grown at Dover, Florida[z]

| Cultivar | Marketable yield[y] (g/plant) Dec. | Jan. | Feb. | Mar. | Total | Weight/fruit[x] (g) |
|---|---|---|---|---|---|---|
| | | | 1997–98 | | | |
| S.Festival | 47b | 90ab | 205ab | 357ab | 700a | 317.6b |
| Sweet Charlie | 91a | 54b | 219a | 257b | 622a | 17.6b |
| Camarosa | 50b | 105a | 167b | 426a | 748a | 20.0a |
| | | | 1998–99 | | | |
| S.Festival | 43b | 62b | 68b | 273b | 446b | 15.9b |
| Sweet Charlie | 36b | 52b | 134a | 289b | 511b | 15.7b |
| Camarosa | 81a | 154a | 110ab | 615a | 961a | 19.6a |

[z]Transplants were obtained from the following nursery locations: 'Strawberry Festival' from Florida in 1997, and New York in 1998; 'Sweet Charlie' from Florida in 1997, and North Carolina in 1998; and 'Camarosa' from North Carolina in 1997, and Canada in 1998. Planting dates were Oct. 9 1997 and Oct. 16 1998.

[y]Values represent mean per plant yield for four 10-plant plots.

[x]Mean fruit weight was determined by dividing total marketable fruit yield per plot by total marketable fruit number per plot.

[w]Mean separation within colulumns and seasons by Fisher's protected least significant difference test, $P \leqq 0.05$.

TABLE 2

Sensory characteristics of 'Strawberry Festival' strawberry fruit compared with those of two standard cultivars grown at Dover, Florida[z]

| Cultivar | Color uniformity[y] | Flavor intensity[y] | Sweetness[y] | Firmness[y] |
|---|---|---|---|---|
| S. Festival | 11.4 (0.35) | 7.5 (0.65) | 7.4 (0.56) | 10.7 (0.95) |
| Sweet Charlie | 9.4 (0.37) | 6.8 (0.79) | 7.6 (0.55) | 6.8 (0.71) |
| Camarosa | 10.5 (0.74) | 6.1 (0.25) | 6.5 (0.34) | 9.3 (0.42) |

[z]Means based on the ratings of 12 to 15 trained panelists who rated samples of fruit from each cultivar three times in 1999. Standard Errors in parenthesis.

[y]Rating scale 1 to 15, with a higher score indicating more uniform color, more strawberry flavor intensity, more sweetness, and more firmness.

TABLE 3

DNA marker analysis[x]

| | Primer B06 | B07 | B14 | X11 | X06 |
|---|---|---|---|---|---|
| | Band number for each primer and DNA pattern | | | | |
| Variety | 1234 | 12 | 12345 | 12 | 12 |
| S. Festival | 0000 | 11 | 00010 | 10 | 10 |
| Rosa Linda | 0001 | 11 | 00000 | 00 | 11 |
| Sweet Charlie | 0101 | 01 | 00111 | 10 | 01 |

TABLE 3-continued

| | DNA marker analysis[x] | | | | |
|---|---|---|---|---|---|
| | Primer | | | | |
| | B06 | B07 | B14 | X11 | X06 |
| | Band number for each primer and DNA pattern | | | | |
| Variety | 1234 | 12 | 12345 | 12 | 12 |
| Camarosa | 1101 | 10 | 10010 | 10 | 11 |
| Oso Grande | 1001 | 11 | 01010 | 11 | 10 |

[z]Random amplified polymorphic DNA (RAPD) patterns were determined using primers B06, B07, B14, X06, and X11 from Operon Technologies, Inc.. Stolon tip DNA's were isolated using DNeasy Plant ™ extraction kit from Qiagen ®, Inc. Amplification reactions were performed in 20 microliter volumes using a procedure adapted from Williams et al.,1990), Nucleic Acids Research 25: 6531–6535. The reagents and conditions included 50 mM Tris (pH 8.3), 0.25 mg/mL bovine serum albumin, 2.1 mM $MgCl_2$, 0.5% Ficoll 400, 1.0 mM tartrazine, 0.2 mM each of dATP, dCTP, dGTP, dTTP, 1.0 mM primer DNA, 0.065 ng strawberry DNA, 1 unit Taq-DNA polymerase (Promega, Inc.). The reaction conditions were 4 minutes at 94° C., then 10 seconds at 94° C., 1 minute at 45° C., 3.5 minutes at 68° C.,then 9 cycles of 10 seconds at 94° C., 1 minute at 45° C. with an incrementation of 0.5 degrees per cycle, 3.5 minutes at 68° C., then 29 cycles of 10 seconds at 94° C., 1 minute at 40° C. and 3.5 minutes at 68° C. with a 10 second extension per cycle. The reactions were incubated in Model PTC-100 thermocycler (MJR, Inc.).

TABLE 3-continued

| | DNA marker analysis[x] | | | | |
|---|---|---|---|---|---|
| | Primer | | | | |
| | B06 | B07 | B14 | X11 | X06 |
| | Band number for each primer and DNA pattern | | | | |
| Variety | 1234 | 12 | 12345 | 12 | 12 |

The reaction products were analyzed with gel electrophoresis using 1.0% agarose 3:1 high resolution blend (AMRESCO, Inc.) in a running buffer of 0.045 M Tri-Borate, 0.001 M EDTA. The separated DNA was detected using ethidium bromide and viewed with a ultra violet transilluminator. Reproducible polymorphic banding from the electrophoresis analysis was observed with the DNA primers. The amplification reactions resulted with variying levels of polymorphism, from 2 to 5 polymorphic bands depending on the primer used. The polymorphic bands were scored as 0 equals absence and 1 equals presence.

I claim:

1. A new and distinct strawberry plant as illustrated and described, characterized by heavy runnering in the fruiting field, and production of fruit that are flavorful, firm fleshed, deep red on the outside, bright red on the inside, conically shaped, and attached to long pedicels, when grown in the Dover/Plant City area of Florida.

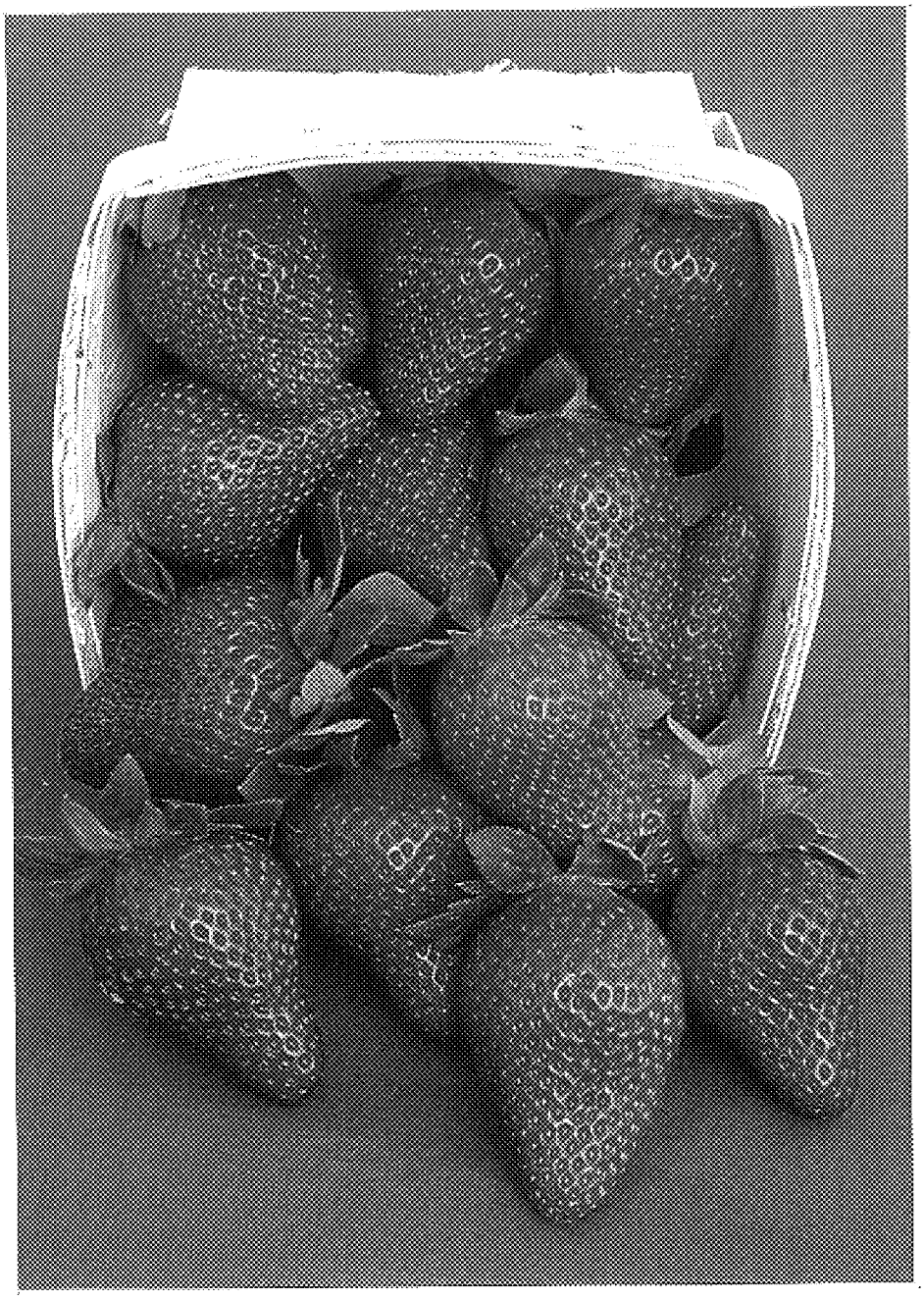

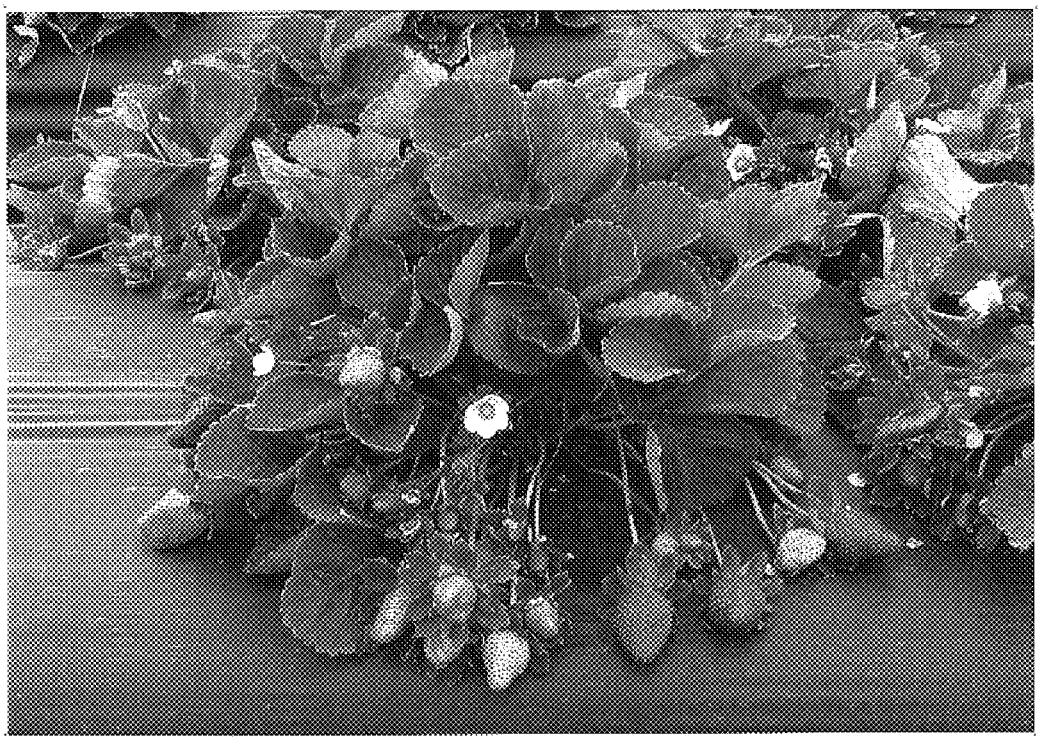

* * * * *